US00PP14524P29

(12) United States Plant Patent
Hanes

(10) Patent No.: US PP14,524 P2
(45) Date of Patent: Feb. 10, 2004

(54) GERANIUM PLANT NAMED 'FREE PINK TWO'

(50) Latin Name: *Pelargonium peltatum*
Varietal Denomination: Free Pink Two

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 52 days.

(21) Appl. No.: 10/397,988

(22) Filed: Mar. 25, 2003

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Jondle & Associates, PC

(57) ABSTRACT

A geranium cultivar particularly distinguished by dark green foliage with light zonation, pink flower color, and semi-double flowers on large umbels, fast rooting and exhibits vigorous growth.

1 Drawing Sheet

Genus and species: *Pelargonium peltatum.*
Variety denomination: 'Free Pink Two'.

BACKGROUND OF THE NEW PLANT

The present invention comprises a new and distinct cultivar of geranium, botanically known as *Pelargonium peltatum*, and hereinafter referred to by the cultivar name 'Free Pink Two'. The new cultivar originated from the cross of a seed parent known as 5165-1 a blue-pink proprietary line unpatented and unnamed ×5146-1 a red proprietary line unpatented and unnamed.

'Free Pink Two' is a product of a planned breeding program intended to create new geranium cultivars with pink colored flowers, semi-double flower form, green foliage, vigorous growth and superior cutting productivity.

The new cultivar was created in 1996 in Gilroy, Calif. and has been repeatedly asexually reproduced by cuttings in Gilroy, Calif., Guatemala and Kenya over a six-year period. It has also been trialed at Gilroy, Calif., Litchfield, Mich. and Andijk, The Netherlands. It has been found to retain its distinctive characteristics through successive asexual propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

The photograph shows umbels and flowers of 'Free Pink Two'.

DESCRIPTION OF THE NEW CULTIVAR

The following detailed descriptions set forth the distinctive characteristics of 'Free Pink Two'. The data which defines these characteristics were collected from asexual reproductions carried out in Gilroy, Calif. The plant history was taken on 10 month old plants blossomed in one-gallon pots in the fall/winter season, in poly-covered greenhouse under natural light in a greenhouse and color readings were taken in the greenhouse in Gilroy, Calif. under natural light.

Plants had been cut back numerous times prior to data readings taken. Color references are primarily to The R.H.S. Colour Chart of The Royal Horticultural Society of London (R.H.S.). Texture description details were observed under a dissecting microscope.

DETAILED BOTANICAL DESCRIPTION

Classification:
*Botanical.*—*Pelargonium peltatum.*
*Commercial.*—Ivy Geranium.
Form: Semi upright and decumbent.
Growth and branching habit: Good vigorous habit, well branched.
Height: From soil level to top of plant (excluding blooms) 15–20 cm; from soil level to top of umbels 20–25 cm.
Width: 50–60 cm if lateral branches are outstretched the width is approximately 140 cm.
Time to produce a finished flowering plant: 8–14 weeks for 4–6 inch pots.
Outdoor plant performance: Good weather tolerance, used in hanging baskets, patio or mixed containers.
Time to initiate roots: 10–28 days.
Root description: White, slightly pubescent, fibrous yet coarse.

The Leaves

Color: Upper side, Little darker than RHS 146A (yellow-green); Underside, RHS 147A (yellow-green) and ribs RHS 144A (yellow-green).
Length: 8.5–9.7 cm.
Width: 8.5–9.0 cm.
Apex description: Acute.
Base description: Cordate.
Shape: Reniform.
Margin: Entire — Ciliate.
Texture: Hirsute of various sizes.
Zonation color: Very very light shade of RHS 200D (brown).
Zonation diameter: 2.0–3.0 cm.
Venation type: Palmate.
Venation color: Little lighter than RHS 146A (yellow-green).
Petiole color: RHS 144A (yellow-green).

Petiole length: 5.0–6.5 cm.
Petiole diameter: 2.0–3.0 cm.
Petiole texture: Villous, short glandular hairs.

The Stem

Color: Between RHS 144A (yellow-green) and RHS 144B (yellow-green).
Length: 50–70 cm.
Internode length: 5.0–6.2 cm.
Texture: Strigulose and some short glandular hairs.

The Bud

Diameter: 0.6–0.8 cm.
Length: 1.1–1.4 cm.
Shape: Elliptic-Oval.
Color when sepals first divide: RHS 50A (red).

The Inflorescence

Peduncle color: RHS 144A (yellow-green).
Peduncle length: 12.0–13.7 cm.
Peduncle diameter: 0.3 cm.
Peduncle texture: Villous and glandular hairs.
Pedicel color: RHS 144A (yellow-green).
Pedicle length: 2.0–2.3 cm.
Pedicel diameter: 0.1–0.15 cm.
Pedicel texture: Villous and glandular hairs.

The Flower

Type: An umbel composed of approximately 5–12 flowers.
Blooming habit: Continuous blooming throughout the growing season. Good floriferousness.
Diameter: 7.5–9.0 cm.
Depth: 4.0–6.5 cm.
Floret form: Polypetalous; 11–16 cm mostly imbricate petals, 2.5 cm petaloids.
Upper petal color: Close to RHS 58C (red-purple), upper 3 petals, macule of RHS 60A (red-purple) and RHS 71B (red-purple); Undersurface, RHS 54B (red) but a little more pink and streaks of RHS 72C (red-purple) basally.
Upper petaloid color: Close to RHS 58C (red-purple).
Lower petal color: Close to RHS 58C (red-purple); Undersurface, RHS 58B (red-purple) but a little more pink and streaks of white basally.
Lower petaloid color: Close to RHS 58C (red-purple).
Color change with age: Colors do not change with age but may change with temperature and time of year.
Floret diameter: 5.0–5.4 cm.
Petal shape: Spathulate.
Petal apex shape: Rounded.
Petal base shape: Acuminate.
Petal margin: Entire.
Petal texture: Papillose.
Flower persistence: An open flower will hold its petals until the flower begins to dehisce or approximately 7–10 days.
Fragrance: None.
Number of sepals: 5, 1 larger than the other, fused at base.
Sepal color: RHS 144A (yellow-green).
Sepal length: 1.4 cm.
Sepal width: 0.3–0.5 cm.
Sepal shape: Linear-Lanceolate.
Sepal apex shape: Acute.
Sepal texture: Short glandular hairs, villous, strigulose.

The Reproductive Organs

Stamens: 4–6, sometimes fused to petaloids.
Filament color: White.
Pollen color: RHS N172A (greyed-orange).
Pistil: 1.
Stigma color: RHS 187B (greyed-purple) lighter.
Style color: White.
Fruit set: Not observed.

Disease and Insect Resistance

Less susceptibility to Oedema.

Comparison with Known Cultivars

'Free Pink Two' differs from the female parent in the following ways: The female parent has less vigorous growth and has a blue pink color verses the pink color of 'Free Pink Two'.

'Free Pink Two' differs from the male parent in the following ways: The male parent grows more upright and has red colored flowers verses pink color of 'Free Pink Two'.

I claim:

1. A new and distinct cultivar of geranium plant as shown and described herein.

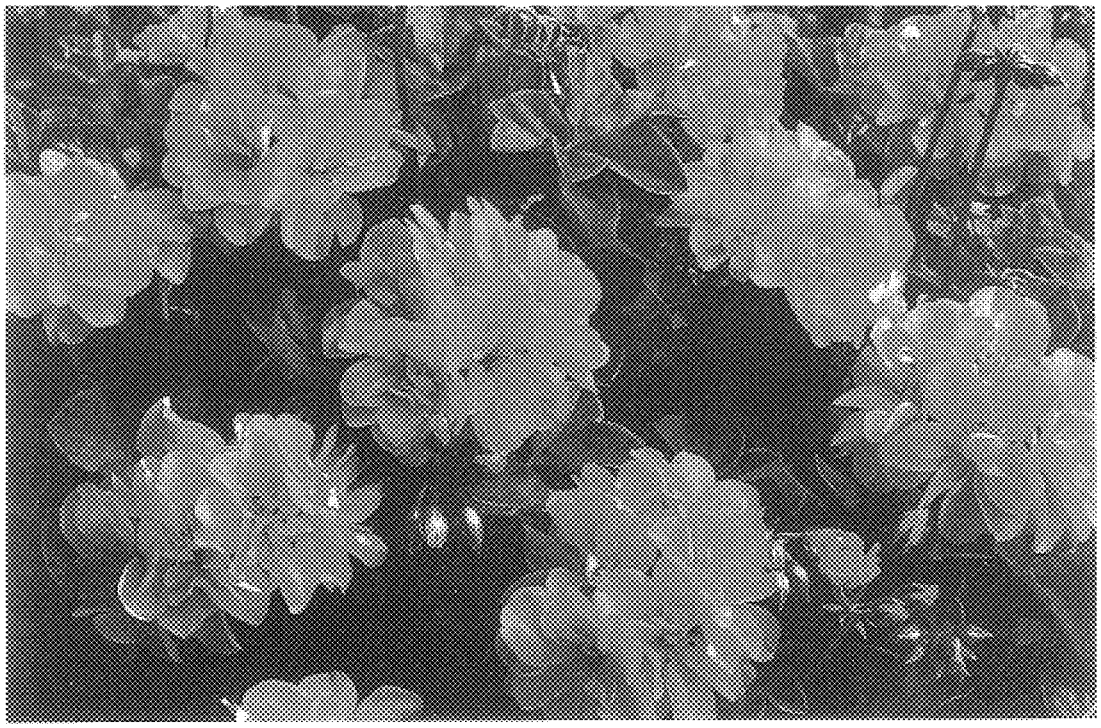

* * * * *